United States Patent
Lee et al.

(10) Patent No.: US 10,596,060 B2
(45) Date of Patent: Mar. 24, 2020

(54) FRAME ASSEMBLY AND MOTION ASSISTANCE APPARATUS INCLUDING THE SAME

(71) Applicants: Samsung Electronics Co., Ltd., Suwon-si, Gyeonggi-do (KR); Korea University of Technology and Education Industry—University Cooperation Foundation, Cheonan-si, Chungcheongnam-do (KR)

(72) Inventors: Youn Baek Lee, Yongin-si (KR); Jeonghun Kim, Suwon-si (KR); Se-Gon Roh, Suwon-si (KR); Jongwon Lee, Suwon-si (KR); Hyun Do Choi, Yongin-si (KR); Yong Jae Kim, Cheonan-si (KR)

(73) Assignees: Samsung Electronics Co., Ltd., Gyeonggi-do (KR); Korea University of Technology and Education Industry-University Cooperation Foundation, Chungcheongnam-do (KR)

( * ) Notice: Subject to any disclaimer, the term of this patent is extended or adjusted under 35 U.S.C. 154(b) by 814 days.

(21) Appl. No.: 15/181,950

(22) Filed: Jun. 14, 2016

(65) Prior Publication Data

US 2017/0151120 A1     Jun. 1, 2017

(30) Foreign Application Priority Data

Nov. 26, 2015    (KR) .................. 10-2015-0166078
Mar. 7, 2016    (KR) .................. 10-2016-0026905

(51) Int. Cl.
*A61H 3/00*     (2006.01)
*A61F 2/60*     (2006.01)
(Continued)

(52) U.S. Cl.
CPC ................ *A61H 3/00* (2013.01); *A61F 2/60* (2013.01); *A61H 1/024* (2013.01); *A61H 1/0244* (2013.01);
(Continued)

(58) Field of Classification Search
CPC combination set(s) only.
See application file for complete search history.

(56) References Cited

U.S. PATENT DOCUMENTS

| 1,705,129 A | 3/1929 | McGoogan |
| 2,115,504 A | 4/1938 | Wallis |

(Continued)

FOREIGN PATENT DOCUMENTS

| CN | 103932870 A | 7/2014 |
| CN | 203924332 U | 11/2014 |

(Continued)

OTHER PUBLICATIONS

Partial European Search Report issued by the European Patent Office dated Mar. 28, 2017 for corresponding EP Patent Application No. 16182240.8.

(Continued)

*Primary Examiner* — Yashita Sharma
(74) *Attorney, Agent, or Firm* — Harness, Dickey & Pierce, P.L.C.

(57) ABSTRACT

A frame assembly including a first longitudinal member, a second longitudinal member spaced apart from the first longitudinal member, a third longitudinal member configured to diagonally connect the first longitudinal member and the second longitudinal member, a plurality of first distance maintaining members configured to connect the first longitudinal member and the second longitudinal member, and a plurality of second distance maintaining members config- (Continued)

ured to connect the second longitudinal member and the third longitudinal member is disclosed.

23 Claims, 19 Drawing Sheets

(51) Int. Cl.
*A61H 1/02* (2006.01)
*A61F 5/01* (2006.01)

(52) U.S. Cl.
CPC .......... *A61H 1/0266* (2013.01); *A61F 5/0102* (2013.01); *A61H 2201/0192* (2013.01); *A61H 2201/1207* (2013.01); *A61H 2201/164* (2013.01); *A61H 2201/165* (2013.01); *A61H 2201/1623* (2013.01); *A61H 2201/1628* (2013.01); *A61H 2201/1676* (2013.01); *A61H 2201/50* (2013.01); *A61H 2201/5007* (2013.01); *A61H 2201/5015* (2013.01); *A61H 2205/081* (2013.01)

(56) References Cited

U.S. PATENT DOCUMENTS

| | | | |
|---|---|---|---|
| 5,462,141 | A | 10/1995 | Taylor |
| 7,416,538 | B2 | 8/2008 | Katoh et al. |
| 7,780,616 | B2 | 8/2010 | Katoh et al. |
| 8,652,075 | B2 | 2/2014 | Takahashi et al. |
| 9,022,958 | B2 * | 5/2015 | Shimizu ............... A61H 1/0244 601/35 |
| 2003/0197110 | A1 | 10/2003 | Cui |
| 2005/0257490 | A1 | 11/2005 | Pryor et al. |
| 2006/0030805 | A1 | 2/2006 | Nordt et al. |
| 2012/0220909 | A1 | 8/2012 | Downing |
| 2016/0045387 | A1 | 2/2016 | Lee et al. |
| 2016/0081870 | A1 | 3/2016 | Lee et al. |
| 2017/0151083 | A1 | 6/2017 | Lee et al. |

FOREIGN PATENT DOCUMENTS

| | | |
|---|---|---|
| CN | 104434470 A | 3/2015 |
| EP | 3 143 969 A1 | 3/2017 |
| FR | 3 013 586 A1 | 5/2015 |
| JP | 2007-152035 A | 6/2007 |
| JP | 2007-307216 A | 11/2007 |
| JP | 2011-139870 A | 7/2011 |
| JP | 4747327 B2 | 8/2011 |
| JP | 2013176429 A | 9/2013 |
| KR | 1020050075953 | 7/2005 |
| KR | 10-1278513 B1 | 6/2013 |
| WO | WO-96/22859 A1 | 8/1996 |
| WO | WO-2010/035706 A1 | 4/2010 |
| WO | WO-2014/163514 A1 | 10/2014 |

OTHER PUBLICATIONS

Extended European Search Report dated Jun. 6, 2017 for corresponding EP Application No. 16182240.8.
Extended European search Report dated Nov. 20, 2019 for corresponding EP Application No. 19182901.9.

* cited by examiner

FRAME ASSEMBLY AND MOTION ASSISTANCE APPARATUS INCLUDING THE SAME

CROSS-REFERENCE TO RELATED APPLICATION

This application claims under 35 U.S.C. § 119 to Korean Patent Application No. 10-2015-0166078 filed on Nov. 26, 2015 and Korean Patent Application No. 10-2016-0026905 filed on Mar. 7, 2016 in the Korean Intellectual Property Office, the entire contents of both of which are incorporated herein by reference in their entirety.

BACKGROUND

1. Field

At least one example embodiment relates to a frame assembly and/or a motion assistance apparatus including the same.

2. Description of the Related Art

Motion assistance apparatuses enabling the elderly and/or patients having joint problems to walk with less effort have been developed. The motion assistance apparatuses increasing muscular strength of human bodies are also desired for various purposes.

SUMMARY

Some example embodiments relate to a frame assembly.

In some example embodiments, the frame assembly may include a first longitudinal member configured to connect to a first object and a second object; a second longitudinal member configured to connect to the first object and the second object such that the second longitudinal member and the first longitudinal member are separated by a distance in a first direction with the first object and the second object therebetween; a third longitudinal member configured to diagonally connect the first longitudinal member and the second longitudinal member; a plurality of first distance maintaining members configured to connect the first longitudinal member and the second longitudinal member; and a plurality of second distance maintaining members configured to connect the second longitudinal member and the third longitudinal member.

In some example embodiments, the frame assembly may include a first end portion, a second end portion and an intermediate portion therebetween such that a stiffness of each of the first end portion and the second end portion is greater than a stiffness of the intermediate portion, and the plurality of first distance maintaining members and the plurality of second distance maintaining members extend in the first direction.

In some example embodiments, a distance between the first longitudinal member and the second longitudinal member increases from the second end portion toward the first end portion.

In some example embodiments, a distance between the second longitudinal member and the third longitudinal member decreases from the second end portion toward the first end portion.

In some example embodiments, an intermediate portion of the first longitudinal member is configured to move relative to an intermediate portion of the second longitudinal member, and the intermediate portion of the second longitudinal member is configured to move relative to an intermediate portion of the third longitudinal member.

In some example embodiments, the plurality of first distance maintaining members are configured to rotate relative to one or more of the first longitudinal member and the second longitudinal member.

In some example embodiments, at least one of the plurality of first distance maintaining members is configured such that end portions thereof are more flexible than an intermediate portion between the end portions.

In some example embodiments, at least one of the plurality of first distance maintaining members is configured such that cross sections of end portions thereof are smaller than a cross section of an intermediate portion between the end portions.

In some example embodiments, a thickness of at least one of the first distance maintaining members is greater than a thickness of each of the first longitudinal member and the third longitudinal members.

In some example embodiments, at least one of the plurality of first distance maintaining members includes a first slider and a second slider, the first slider configured to slide relative to the second slider.

In some example embodiments, the first slider includes a first slider body connected to the first longitudinal member, and a first fitting portion on the first slider body, the first slider configured to extend toward the second longitudinal member; and the second slider include a second slider body connected to the second longitudinal member, and a second fitting portion on the second slider body, the second slider body configured to extend toward the first longitudinal member and the second fitting portion configured to fit in the first fitting portion.

In some example embodiments, a width of the first fitting portion increases as a distance in a direction away from the first slider body increases.

In some example embodiments, at least one of the plurality of distance maintaining members includes a separation preventing member configured to resist separation of the first slider and the second slider.

In some example embodiments, a length of each of the plurality of first distance maintaining members in the first direction is shorter than a length of the first longitudinal member and the second longitudinal member in a second direction.

In some example embodiments, among the plurality of first distance maintaining members, a distance between two neighboring ones of the first distance maintaining members is shorter than a length in the first direction of a shorter one of the two neighboring ones of the first distance maintaining members.

In some example embodiments, at least one of the plurality of first distance maintaining members includes a material that is stiffer than a material included in the first longitudinal member and the second longitudinal member.

In some example embodiments, at least one of the plurality of first distance maintaining members includes a first end fixed to the first longitudinal member, and a second end fixed to the second longitudinal member.

In some example embodiments, at least one of the plurality of first distance maintaining members is rotatably fixed to one of the first longitudinal member and the second longitudinal member.

Some example embodiments relate to a motion assistance apparatus.

In some example embodiments, the motion assistance apparatus may include a back support configured to support a back of a user; a driver on one side of a joint of the user; and a frame assembly having a first end portion, a second end portion and an intermediate portion therebetween, the first end portion configured to connect to the driver and the second end portion configured to connect to the back support, the first end portion and the second end portion of the frame assembly each having a stiffness greater than a stiffness of the intermediate portion.

In some example embodiments, the frame assembly includes a first longitudinal member and a second longitudinal member each configured to connect to the back support and the driver; a plurality of first distance maintaining members configured to connect the first longitudinal member and the second longitudinal member in the first direction such that the second longitudinal member maintains a distance in a first direction from the first longitudinal member with the back support and the driver therebetween; a third longitudinal member configured to connect the back support and the driver; and a plurality of second distance maintaining members configured to connect the second longitudinal member and the third longitudinal member such that the third longitudinal member maintains a distance from the second longitudinal member.

In some example embodiments, a longitudinal direction of the plurality of first distance maintaining members intersects a longitudinal direction of the plurality of second distance maintaining members.

In some example embodiments, the frame assembly includes a first longitudinal member configured to connect to back support and the driver; a second longitudinal member configured to connect to back support and the driver such that the second longitudinal member and the first longitudinal member are separated by a distance in a first direction; and a third longitudinal member configured to diagonally connect the first longitudinal member and the second longitudinal member.

In some example embodiments, the motion assistance apparatus may include a control clamp configured to control an insertion length of at least one of the first longitudinal member and the second longitudinal member into to the back support.

In some other example embodiments, the motion assistance apparatus may include a driver configured to generate a driving force; a support configured to rotate in response to a driving force from the drive; and a fixing device configured to attach to a waist of the user, the fixing device including a waist band configured to enclose a waist of a user and support the driver mounted thereto, the waist band including a front waist band and a rear waist band having ends thereof connected to ends of frame assemblies such that a stiffness of the ends of the frame assemblies is greater than a stiffness of a central portion of the frame assemblies between the ends thereof.

In some example embodiments, the front waist band is configured to support the driver mounted thereto such that one of the ends of the frame assembly is connected to the driver.

In some example embodiments, the frame assemblies each include a first longitudinal member configured to connect an upper portion of the rear waist band to an upper portion of the driver; a second longitudinal member configured to connect a bottom portion of the rear waist band and a bottom portion of the driver such that the second longitudinal member and the first longitudinal member are separated by a distance; and a third longitudinal member configured to connect the upper portion of a first one of the rear waist band and the front waist band to a lower portion of a second one of the rear waist band and the front waist band such that the third longitudinal member diagonally connects the first longitudinal member and the second longitudinal member.

In some example embodiments, in each of the frame assemblies, a distance between the first longitudinal member and the second longitudinal member increases from the rear waist belt toward the front waist belt.

In some example embodiments, in each of the frame assemblies, a distance between the second longitudinal member and the third longitudinal member decreases from the rear waist belt toward the front waist belt.

In some example embodiments, the frame assemblies each further include a plurality of first distance maintaining members configured to connect the first longitudinal member and the second longitudinal member such that the second longitudinal member maintains the distance from the first longitudinal member; and a plurality of second distance maintaining members configured to connect the second longitudinal member and the third longitudinal member in a first direction such that the third longitudinal member maintains a distance from the second longitudinal member.

In some example embodiments, each of the frame assemblies includes a plurality of hollow flexible tubes configured to flex while maintaining a fixed distance therebetween.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
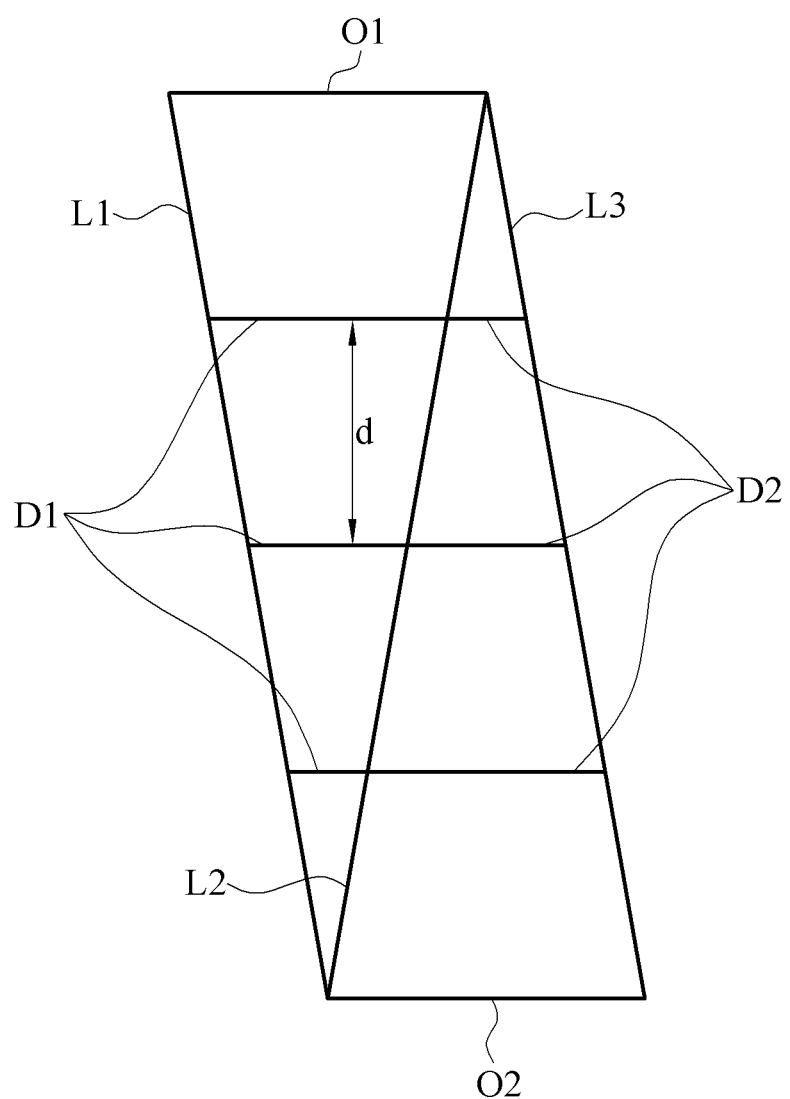
FIG. 1 illustrates an example of a frame assembly according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be a computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
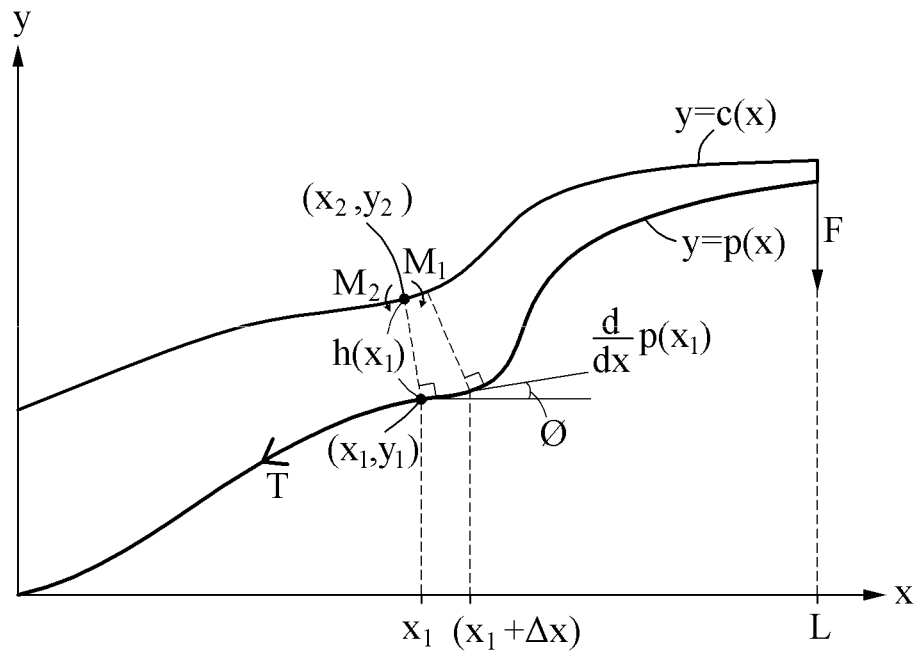
FIG. 2 illustrates a method of determining a shape of a frame assembly according to at least one example embodiment.

FIG. 1 illustrates an example of a frame assembly according to at least one example embodiment, and FIG. 2 illustrates a method of determining a shape of the frame assembly according to at least one example embodiment.

Referring to FIGS. 1 and 2, a frame assembly may include at least three longitudinal members, for example, a first longitudinal member L1, a second longitudinal member L2, and a third longitudinal member L3 each configured to connect a first object O1 and a second object O2, and a plurality of first distance maintaining members D1 and a plurality of second distance maintaining members D2 each configured to connect two neighboring longitudinal members among the at least three longitudinal members. One of the at least three longitudinal members L1-L3 may have an intermediate portion configured to move relative to an intermediate portion of another longitudinal member. The distance maintaining members D1, D2 may each allow two neighboring longitudinal members to have a desired (or, alternatively, a predetermined) shape based on a degree to which the two neighboring longitudinal members are bent. For example, the distance maintaining members D1, D2 may prevent buckling of their two neighboring longitudinal members.

The at least three longitudinal members L1-L3 may be formed of a flexible material. The at least three longitudinal members may be formed of a material, for example, synthetic resins having a flexibility and a stiffness sufficient to prevent the buckling which may occur due to a self-weight. For example, the at least three longitudinal members may each have a flexural stiffness of 10% or less with respect to a longitude stiffness.

Both end portions of the first longitudinal member L1 may be fixed to the first object O1 and the second object O2, respectively. Similarly, both end portions of each of the second longitudinal member L2 and the third longitudinal member L3 may be fixed to the first object O1 and the second object O2, respectively.

A distance between the first longitudinal member L1 and the second longitudinal member L2 may decrease from the first object O1 toward the second object O2 and thus, an interval between the first longitudinal member L1 and the second longitudinal member L2 may be provided in an initial shape of a reversed triangle as illustrated in FIG. 1. In contrast, a distance between the second longitudinal member L2 and the third longitudinal member L3 may increase from the first object O1 toward the second object O2 and thus, an interval between the second longitudinal member L2 and the third longitudinal member L3 may be provided in an initial shape of a triangle. For example, the first longitudinal member L1 and the third longitudinal member L3 may be spaced apart from each other to connect the first object O1 and the second object O2. The second longitudinal member L2 may diagonally connect the first longitudinal member L1 and the third longitudinal member L3 and thus, the frame assembly may be provided in an initial shape of a parallelogram overall.

An interval increasing as two neighboring longitudinal members of the at least three longitudinal members separate from a connected object may be determined as shown in a graph of FIG. 2. Hereinafter, an interval between the second longitudinal member L2 and the third longitudinal member L3 will be described as an example. Unless otherwise mentioned, the descriptions of the interval between the second longitudinal member L2 and the third longitudinal member L3 may be applicable to an interval between the first longitudinal member L1 and the second longitudinal member L2. In the graph of FIG. 2, a y-intercept represents a portion at which the second object O2 is in contact with each of the third longitudinal member L3 and the second longitudinal member L2. Based on the graph of FIG. 2, an interval $h(x)$ between the third longitudinal member L3 and the second longitudinal member L2 may be determined. Here, the interval $h(x)$ may prevent the third longitudinal member L3 from being buckled when a force F is applied to the first object O1. For example, a condition of the interval $h(x)$ that sets a sum of moments applied to the third longitudinal member L3 to be zero may be determined.

A point of the third longitudinal member L3 that meets a normal line at a point $(x_1, y_1)$ of the second longitudinal member L2 may be a point $(x_2, y_2)$. Moments applied to the point $(x_2, y_2)$ may include a moment $M_1$ of the force F and a moment $M_2$ applied to the second longitudinal member L2 by a tensile force T. In this example, a tensile force applied to the third longitudinal member L3 may not apply a moment to the point $(x_2, y_2)$ and thus, may not be considered. The moments $M_1$ and $M_2$ may be calculated, as shown in Equations 1 and 2, respectively.

$$M_1 = F(L - x_1 + h(x_1)\sin \Phi) \quad \text{[Equation 1]}$$

$$M_2 = Th(x_1) \quad \text{[Equation 2]}$$

An interval $h(x_1)$ that sets a sum of moments applied to the point $(x_2, y_2)$ to be zero may be determined as shown in Equation 3. Thus, when the same condition is applied to the moment $M_1$ and the moment $M_2$, the interval $h(x_1)$ may be determined as shown in Equation 3.

$$h(x_1) = \frac{F(L-x_1)}{T - F\sin\Phi} \qquad \text{[Equation 3]}$$

In Equation 3, Φ denotes an angle between a tangent line with respect to a point of the second longitudinal member L2 and an x axis. In this example, when p(x) denotes a height of the second longitudinal member L2, y=p(x) may be a function that determines a shape of the second longitudinal member L2. Similarly, c(x) denotes a height of the third longitudinal member L3 and thus, y=c(x) may be a function that determines a shape of the third longitudinal member L3. A relationship between Φ and p(x) may be expressed by Equation 4.

$$\tan\Phi = \frac{d}{dx}p(x) \qquad \text{[Equation 4]}$$

Based on Equation 4, Equation 3 may be expressed as Equation 5.

$$h(x_1) = \frac{F(L-x_1)}{T - F\sin\left(a\tan\left(\frac{d}{dx}p(x_1)\right)\right)} \qquad \text{[Equation 5]}$$

Equation 5 may be generalized as an equation with respect to a predetermined point (x, y) of the second longitudinal member L2 as shown in Equation 6.

$$h(x) = \frac{F(L-x)}{T - F\sin\left(a\tan\left(\frac{d}{dx}p(x)\right)\right)} \qquad \text{[Equation 6]}$$

In Equation 6, a relationship between T and F may be calculated when the function that determines the shape of the second longitudinal member L2, y=p(x) is provided. F denotes a force applied to the first object O1, and may be predetermined by a user or a designer. Thus, when the function y=p(x) is provided, a shape of the third longitudinal member L3 to be spaced apart from the second longitudinal member L2 at the interval h(x) may be determined. In the foregoing example of Equation 6, it is understood that the interval between the third longitudinal member L3 and the second longitudinal member L2 is determined proportionally to a distance in a direction perpendicular to a direction of force applied to the first object O1.

Also, in an example of FIG. 2, it is understood that the frame assembly has a two-dimensional (2D) shape projected onto one plane in a direction perpendicular to a direction in which a force is applied. When the frame assembly is determined using the method as described above, the frame assembly may not be bent and transmit a force intactly although a force is applied to the first object O1. In this example, a plurality of distance maintaining members may allow the frame assembly to be affected by a tension-compression and thus, a stiffness of an end of the frame assembly may increase.

When the frame assembly is determined based on Equation 6, the frame assembly may not be bent and intactly transmits the force. In practice, due to deformation caused by, for example, manufacturing tolerance and assembly tolerance between elements of the frame assembly, a slight variation may occur when the force is applied to the first object O1. Irrespective the aforementioned influences, both end portions of the frame assembly may each have a stiffness greater than that of an intermediate portion with respect to the force.

The description provided above is merely an example of a method of determining an interval between two neighboring longitudinal members of the at least three longitudinal members. Therefore, example embodiments are not limited thereto.

The first distance maintaining member D1 may rotate, slide, or bend relative to the first longitudinal member L1 and the second longitudinal member L2. Based on such structure, an intermediate portion of the first longitudinal member L1 and an intermediate portion of the second longitudinal member L2 may move relative to each other. The first distance maintaining member D1 may prevent the buckling of the first longitudinal member L1 and/or the second longitudinal member L2.

The first distance maintaining member D1 may be shorter than the first longitudinal member L1 and the second longitudinal member L2. Both end portions of the first distance maintaining member D1 may be fixed to the first longitudinal member L1 and the second longitudinal member L2, respectively. To increase the flexural rigidity of the frame assembly, a distance d between two neighboring first distance maintaining members D1 may be shorter than a length of a shorter one of the two first distance maintaining members D1. Also, the plurality of first distance maintaining members D1 may be formed of a stiffer material when compared to the first longitudinal member L1 and the second longitudinal member L2.

The plurality of second distance maintaining members D2 may each have both end portions to which the second longitudinal member L2 and the third longitudinal member L3 are fixed such that the second longitudinal member L2 and the third longitudinal member L3 move relative to each other. Unless otherwise mentioned, the descriptions of the first distance maintaining member D1 may be applicable to the second distance maintaining member D2.

Figure 3:
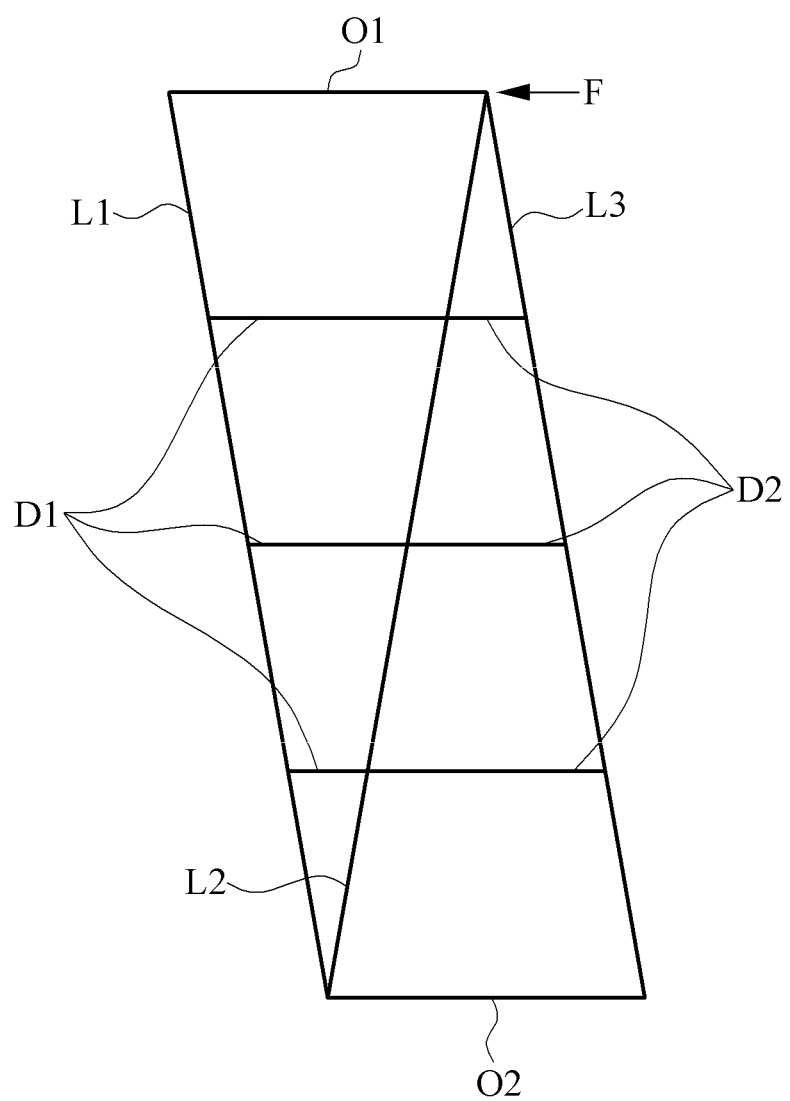
FIG. 3 illustrates an example of a frame assembly with an end portion to which a force is applied according to at least one example embodiment.
Figure 4:
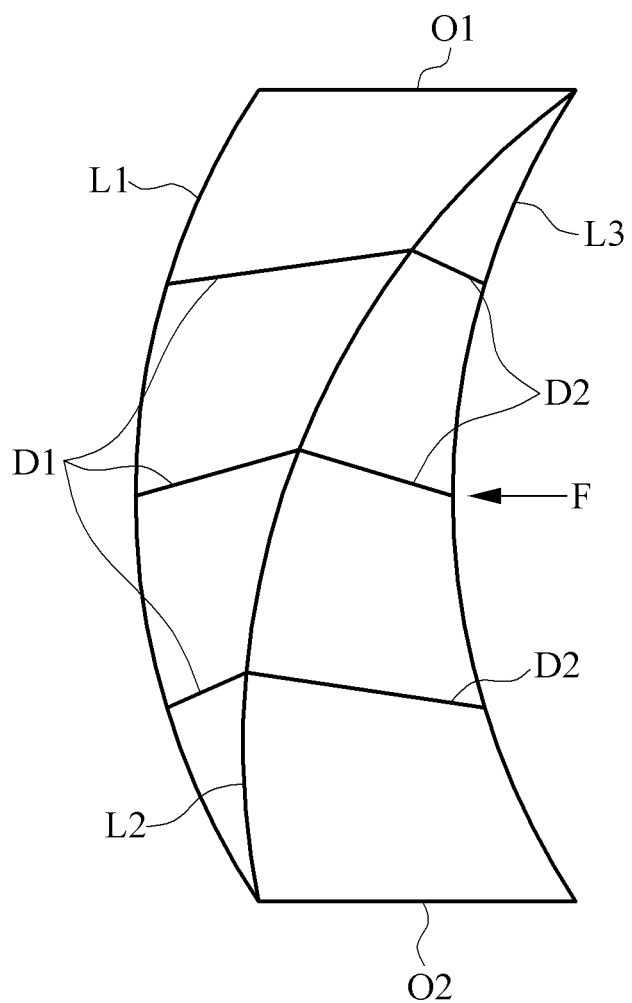
FIG. 4 illustrates an example of a frame assembly with an intermediate portion to which a force is applied according to at least one example embodiment.

FIG. 3 illustrates an example of a frame assembly with an end portion to which a force is applied according to at least one example embodiment, and FIG. 4 illustrates an example of the frame assembly with an intermediate portion to which a force is applied according to at least one example embodiment. FIGS. 3 and 4 illustrate an example in which the first object O1 is a free end and the second object O2 is a fixed end.

As illustrated in FIG. 3, since the frame assembly has a stiffness with respect to a force applied to an end portion, an actual deformation may not occur when the force F is applied to the first object O1 in practice.

In FIG. 4, the frame assembly may have a flexibility with respect to a force applied to an intermediate portion. Thus, when the force F is applied to the intermediate portion in a lateral direction, the first longitudinal member L1, the second longitudinal member L2, and the third longitudinal member L3 may be bent by the force F. In this example, among at least three longitudinal members, two neighboring longitudinal member may move relative to each other while maintaining a distance between the two neighboring longitudinal members using a distance maintaining member, for example, the first distance maintaining member D1 and the second distance maintaining member D2 connecting the two neighboring longitudinal members. When the aforementioned deformation occurs, a relative angle between the first object O1 and the second object O2 may also be maintained (or, alternatively, remain constant) using the first distance maintaining member D1 and the second distance maintaining member D2. For example, the first longitudinal member L1 and the third longitudinal member L3 may be bent in the same shape.

Figure 5:
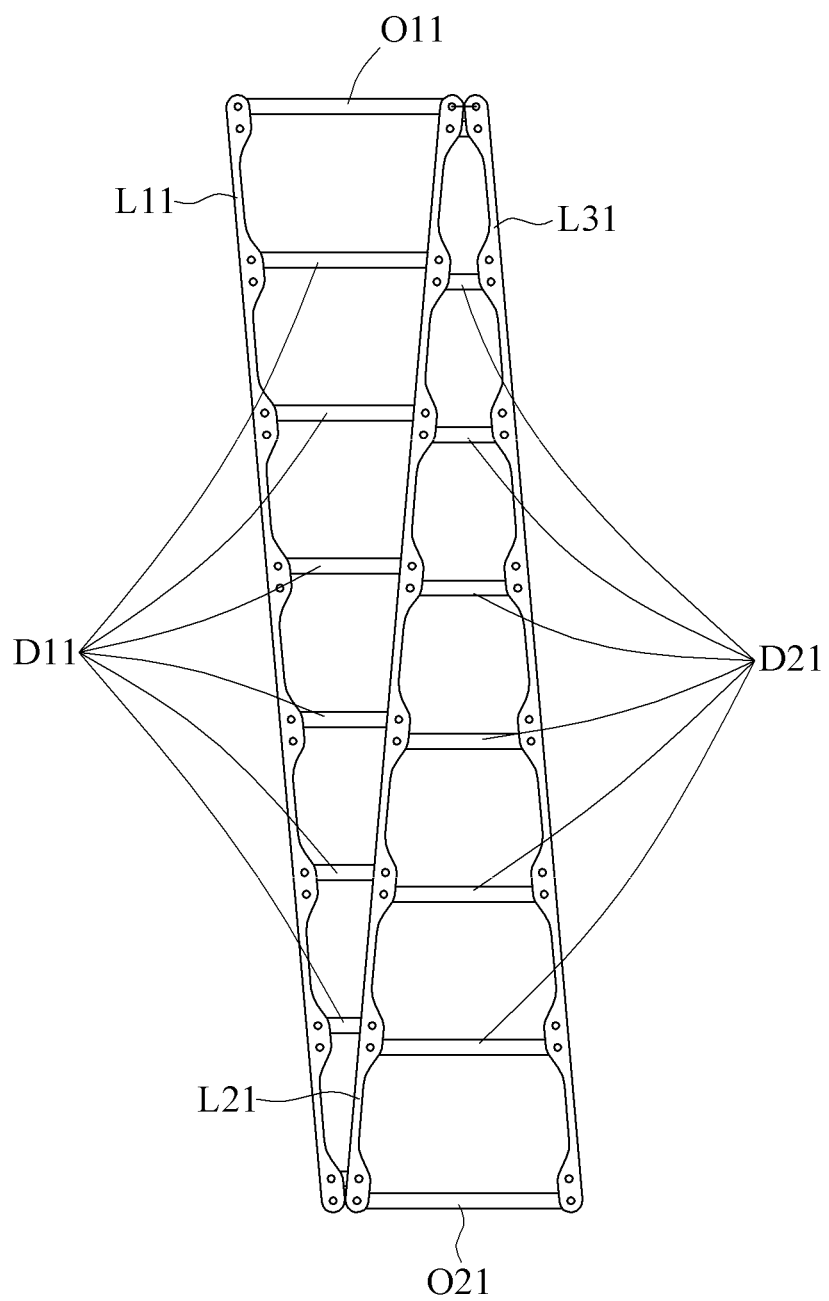
FIGS. 5 through 7 illustrate another example of a frame assembly according to at least one example embodiment.
Figure 6:
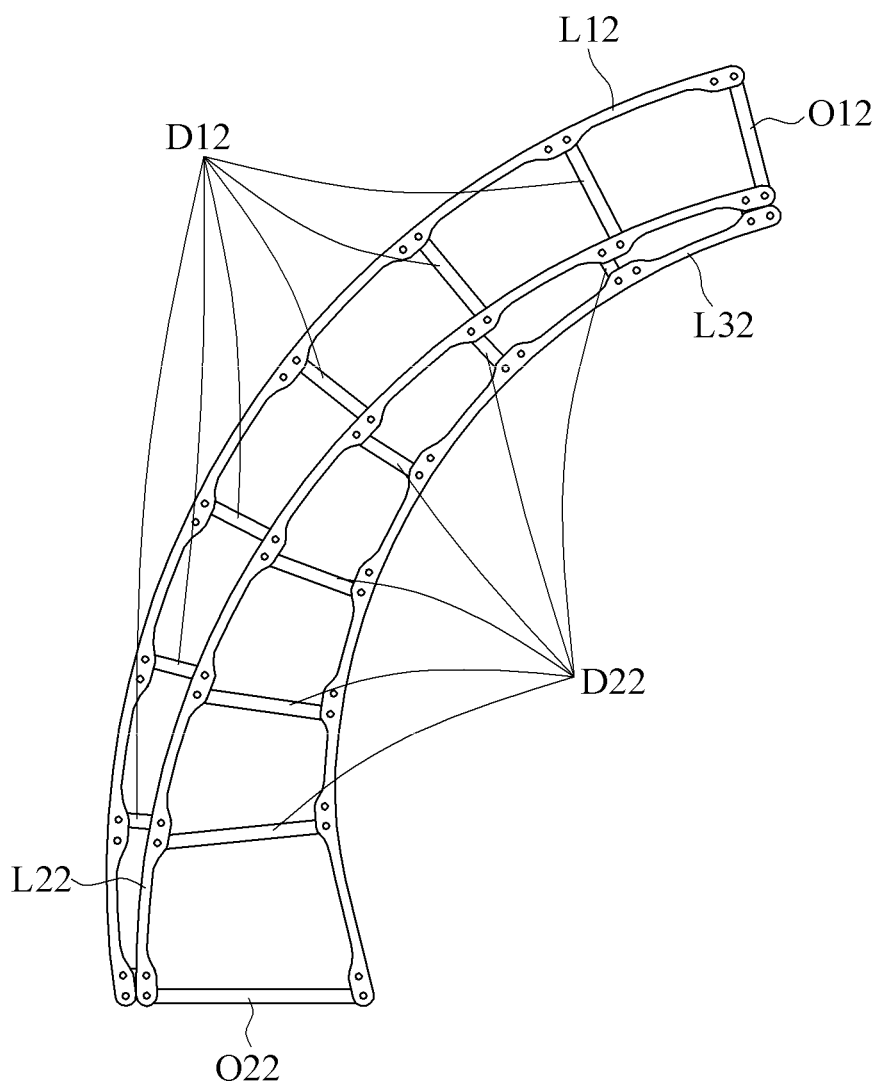
Figure 7:
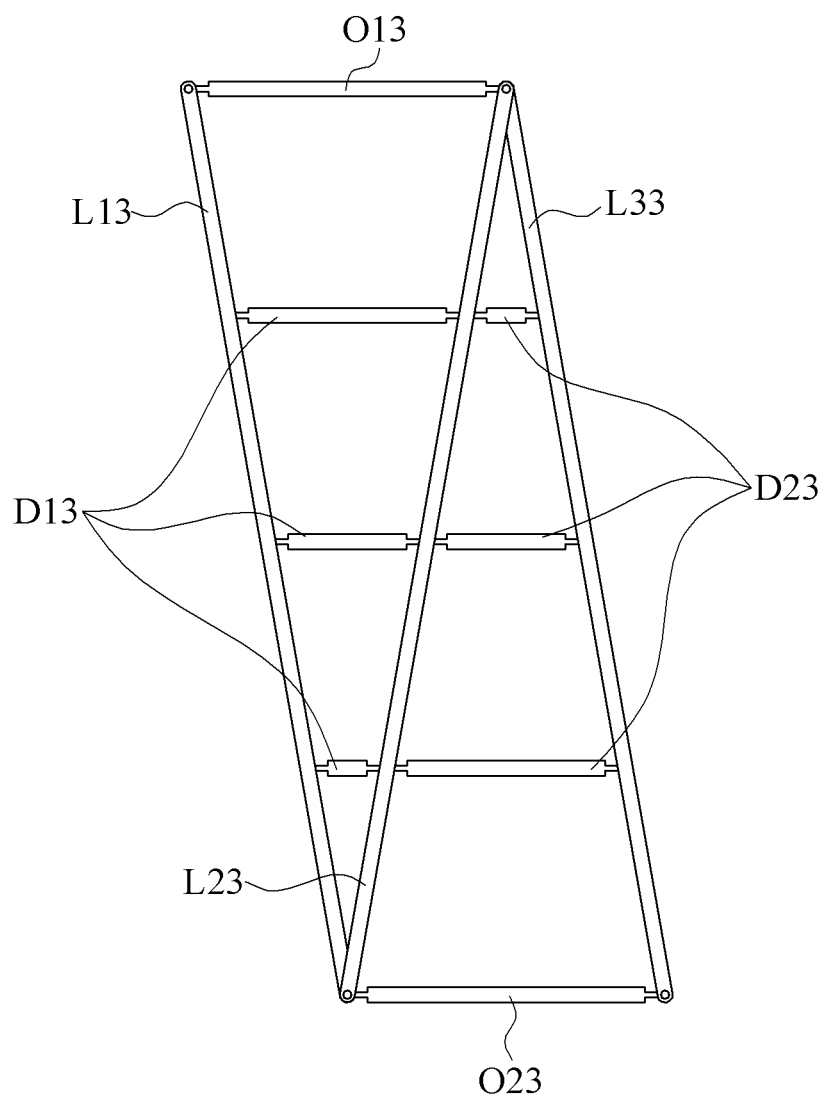

FIGS. 5 through 7 illustrate another example of a frame assembly according to at least one example embodiment.

Referring to FIG. 5, a frame assembly may include a first object O11, a second object O21, a first longitudinal member L11, a second longitudinal member L21, a third longitudinal member L31, a first distance maintaining member D11, and a second distance maintaining member D21.

The first distance maintaining member D11 may be formed of a non-rigid material and configured in a non-rigid structure. Both end portions or one end portion of the first distance maintaining member D11 may be rotatably fixed to the first longitudinal member L11 and/or the second longitudinal member L21. Based on the aforementioned structure, an intermediate portion of the first longitudinal member L11 and an intermediate portion of the second longitudinal member L21 may move relative to each other. Similarly, the second distance maintaining member D21 may be formed of a non-rigid material and configured in a non-rigid structure. Also, both end portions end portions or one end portion of the first distance maintaining member D11 may be rotatably fixed to the second longitudinal member L21 and/or the third longitudinal member L31. FIG. 5 illustrates an example in which both end portions of each of the first distance maintaining member D11 and the second distance maintaining member D21 are rotatably attached to two neighboring longitudinal members through a hinge connection, respectively.

A longitudinal direction of the first distance maintaining member D11 and a longitudinal direction of the second distance maintaining member D21 may be determined based on a desired force support direction. For example, the longitudinal direction of the first distance maintaining member D11 may be the same as the longitudinal direction of the second distance maintaining member D21.

Referring to FIG. 6, a frame assembly may include a first object O12, a second object O22, a first longitudinal member L12, a second longitudinal member L22, a third longitudinal member L32, a first distance maintaining member D12, and a second distance maintaining member D22.

A longitudinal direction of the first distance maintaining member D12 and a longitudinal direction of the second distance maintaining member D22 may be determined based on a desired force support direction. As illustrated in the drawing, the longitudinal direction of the first distance maintaining member D12 and the longitudinal direction of the second distance maintaining member D22 may intersect each other. Also, the first longitudinal member L12, the second longitudinal member L22, and the third longitudinal member L32 may have various initial shapes as necessary.

Referring to FIG. 7, a frame assembly may include a first object O13, a second object O23, a first longitudinal member L13, a second longitudinal member L23, a third longitudinal member L33, a first distance maintaining member D13, and a second distance maintaining member D23.

A portion of the first distance maintaining member D13 may be formed of a flexible material and configured in a flexible structure. Thus, the portion of the first distance maintaining member D13 may be bent with respect to the first longitudinal member L13 and the second longitudinal member L23. Based on the aforementioned structure, an intermediate portion of the first longitudinal member L13 and an intermediate portion of the second longitudinal member L23 may move relative to each other. For example, in the first distance maintaining member D13, both end portions may each have a cross section one-fifth (⅕) to one-tenth (1/10) a cross section of the intermediate portion. The intermediate portion may be formed of a rigid material and configured in a rigid structure.

The first distance maintaining member D13 may be thicker than two neighboring longitudinal members, for example, the first longitudinal member L13 and the second longitudinal member L23. The first distance maintaining member D13 may have a thickness sufficient to prevent buckling of the first longitudinal member L13 and the second longitudinal member L23, for example, a thickness 10 to 100 times the thicknesses of the first longitudinal member L13 and the second longitudinal member L23.

Similarly, the second distance maintaining member D23 may be formed of a flexible material and configured in a flexible structure. Thus, the second distance maintaining member D23 may be bent with respect to the second longitudinal member L23 and the third longitudinal member L33.

Figure 8:
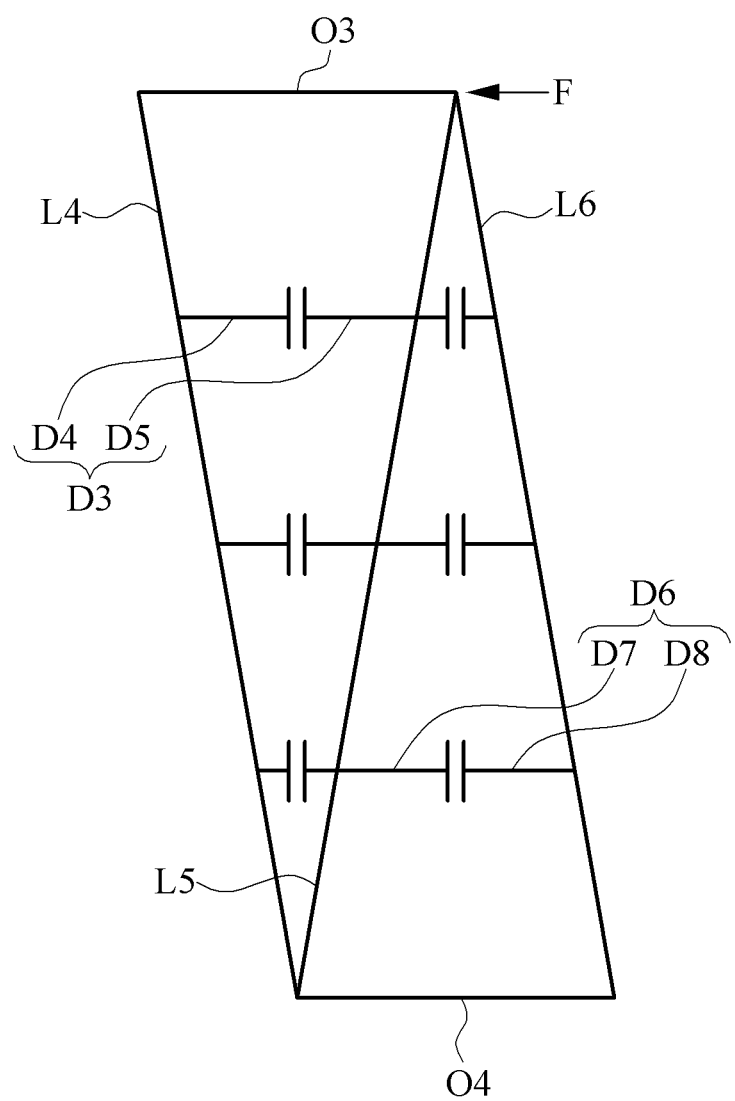
FIG. 8 illustrates still another example of a frame assembly according to at least one example embodiment.
Figure 9:
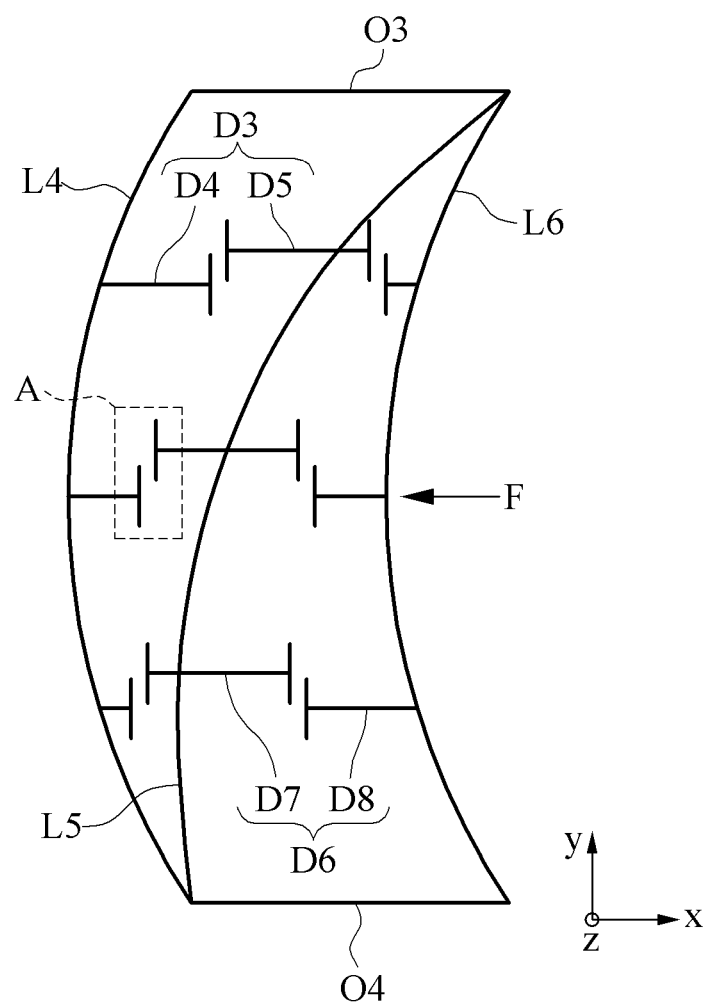
FIG. 9 illustrates another example of a frame assembly with an intermediate portion to which a force is applied according to at least one example embodiment.

FIG. 8 illustrates still another example of a frame assembly according to at least one example embodiment, and FIG. 9 illustrates another example of a frame assembly with an intermediate portion to which a force is applied according to at least one example embodiment.

Referring to FIGS. 8 and 9, a frame assembly may include a first object O3, a second object O4, a first longitudinal member L4, a second longitudinal member L5, a third longitudinal member L6, a first distance maintaining member D3, and a second distance maintaining member D6.

The first distance maintaining member D3 may include a first slider D4 and a second a slider D5 configured to slide relative to each other. The second distance maintaining member D6 may include a third slider D7 and a fourth a slider D8 configured to slide relative to each other.

As illustrated in FIG. 8, since the frame assembly has a stiffness with respect to a force applied to an end portion, an actual deformation may not occur when a force F is applied to the first object O3 in practice.

In FIG. 9, the frame assembly may have a flexibility with respect to a force applied to an intermediate portion. Thus, when the force F is applied to the intermediate portion in a lateral direction, the first longitudinal member L4, the second longitudinal member L5, and the third longitudinal member L6 may be bent by the force F. In this example, among the three longitudinal members, two neighboring longitudinal member may partially slide relative to each other while maintaining a distance between the two neighboring longitudinal members using a distance maintaining member, for example, the first distance maintaining member D3 and the second distance maintaining member D6, connecting the two neighboring longitudinal members. When the aforementioned deformation occurs, a relative angle between the first object O3 and the second object O4 may also be maintained using the first distance maintaining member D3 and the second distance maintaining member D6. For example, the first longitudinal member L4 and the third longitudinal member L6 may be bent in the same shape.

Figure 10:
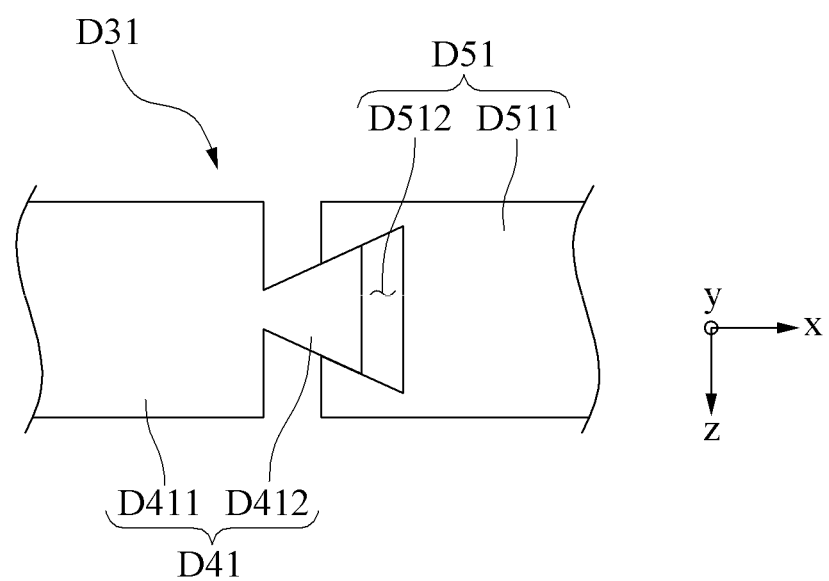
FIGS. 10 through 12 illustrate an example of distance maintaining members according to at least one example embodiment.
Figure 11:
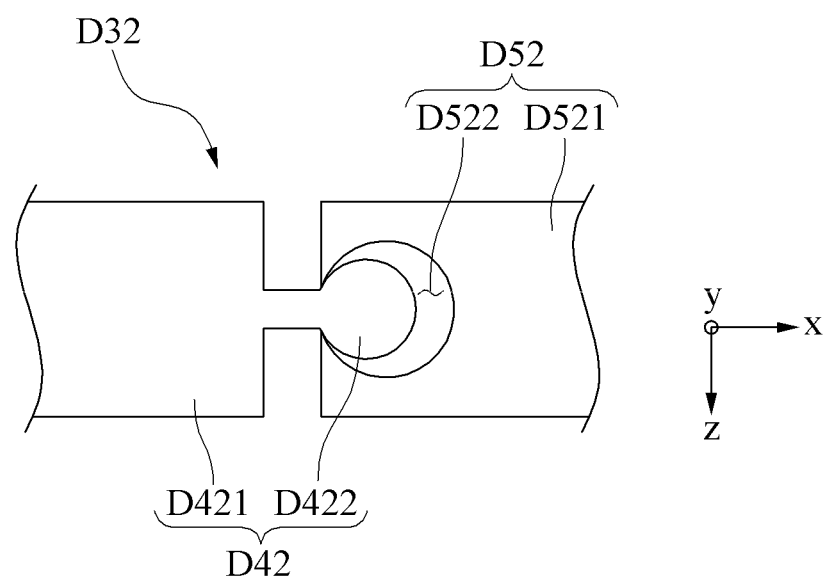
Figure 12:
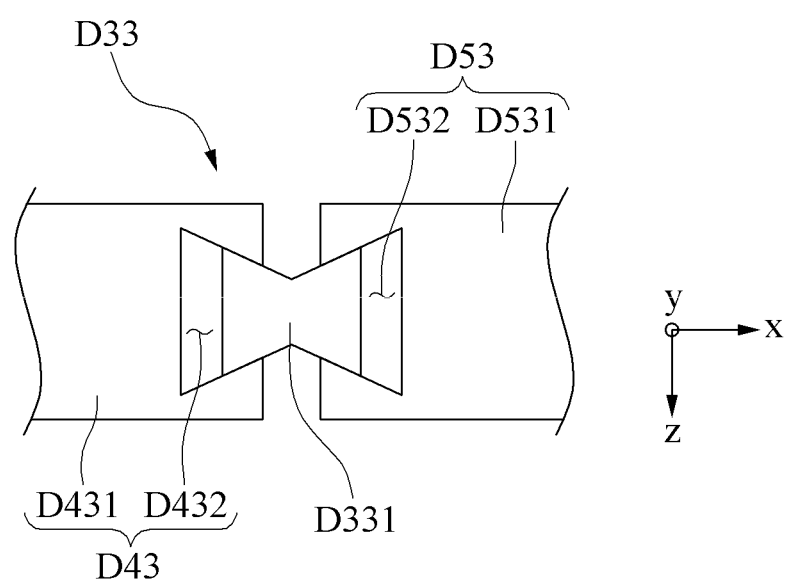

FIGS. 10 through 12 illustrate an example of distance maintaining members according to at least one example embodiment. It is understood that FIGS. 10 through 12 illustrates a portion A of FIG. 9 viewed in a downward direction, for example, a negative direction of a y axis. A structure of a first distance maintaining member will be described with reference to FIGS. 10 through 12, and the descriptions of the structure of the first distance maintaining member may also be applicable to a second distance maintaining member.

Referring to FIG. 10, a first distance maintaining member D31 may include a first slider D41 and a second slider D51 configured to slide relative to the first slider 41.

The first slider D41 may include a first slider body D411 including a non-rigid material and a first fitting portion D412 formed on the first slider body D411. The first slider body D411 may be connected to a first longitudinal member L4 and configured to extend toward a second longitudinal member L5.

The second slider D51 may include a second slider body D511 including a non-rigid material and a second fitting portion D512 fitted in the first fitting portion D412. The second slider body D511 may be connected to the second longitudinal member L5 and configured to extend toward the first longitudinal member L4.

The first slider body D411 and the second slider body D511 may be used to prevent buckling of the first longitudinal member L4 and the second longitudinal member L5 in a direction in which a distance between the first longitudinal member L4 and the second longitudinal member L5 decreases.

One of the first fitting portion D412 and the second fitting portion D512 may protrude and the other may be recessed. By fitting first fitting portion D412 and the second fitting portion D512, the first slider D4 and the second slider D51 may slide relative to each other without separation. The first fitting portion D412 may include a portion with a width increasing as a distance from the first slider body D411 decreases. The first fitting portion D412 may include a cross section that expands in a protruding direction, for example, a dovetail shape. The second fitting portion D512 may include a groove having a cross section expands in a recessed direction.

Referring to FIG. 11, a first distance maintaining member D32 may include a first slider D42 including a first slider body D421 including a non-rigid material and a first fitting portion D422, and a second slider D52 including a second slider body D521 including a non-rigid material and a second fitting portion D522.

The first fitting portion D422 may include a portion with a width increasing as a distance from the first slider body D421 increases. For example, a cross section of the first fitting portion D422 may correspond to a circular shape, and a cross section of the second fitting portion D422 may correspond to a groove having two edges, each bent inwardly.

Referring to FIG. 12, a first distance maintaining member D33 may include a first slider D43 including a first slider body D431 including a non-rigid material and a first fitting portion D432, a second slider D53 including a second slider body D531 including a non-rigid material and a second fitting portion D532, and a separation preventing member D331.

The separation preventing member D331 may prevent a separation between the first slider D43 and the second slider D53. One side of the separation preventing member D331 may be fastened to the first fitting portion D432, and slide with respect to the first fitting portion D432. For example, the one side of the separation preventing member D331 may have a reversed trapezoidal shape including a portion with a width increasing in a direction toward the first slider D43. Similarly, another side of the separation preventing member D331 may be fastened to the second fitting portion D532. The one side and the other side of the separation preventing member D331 may be provided in a shape of two combined reversed trapezoids including portions with widths increasing from a center toward the two sliders D43 and D53, respectively.

Figure 13:
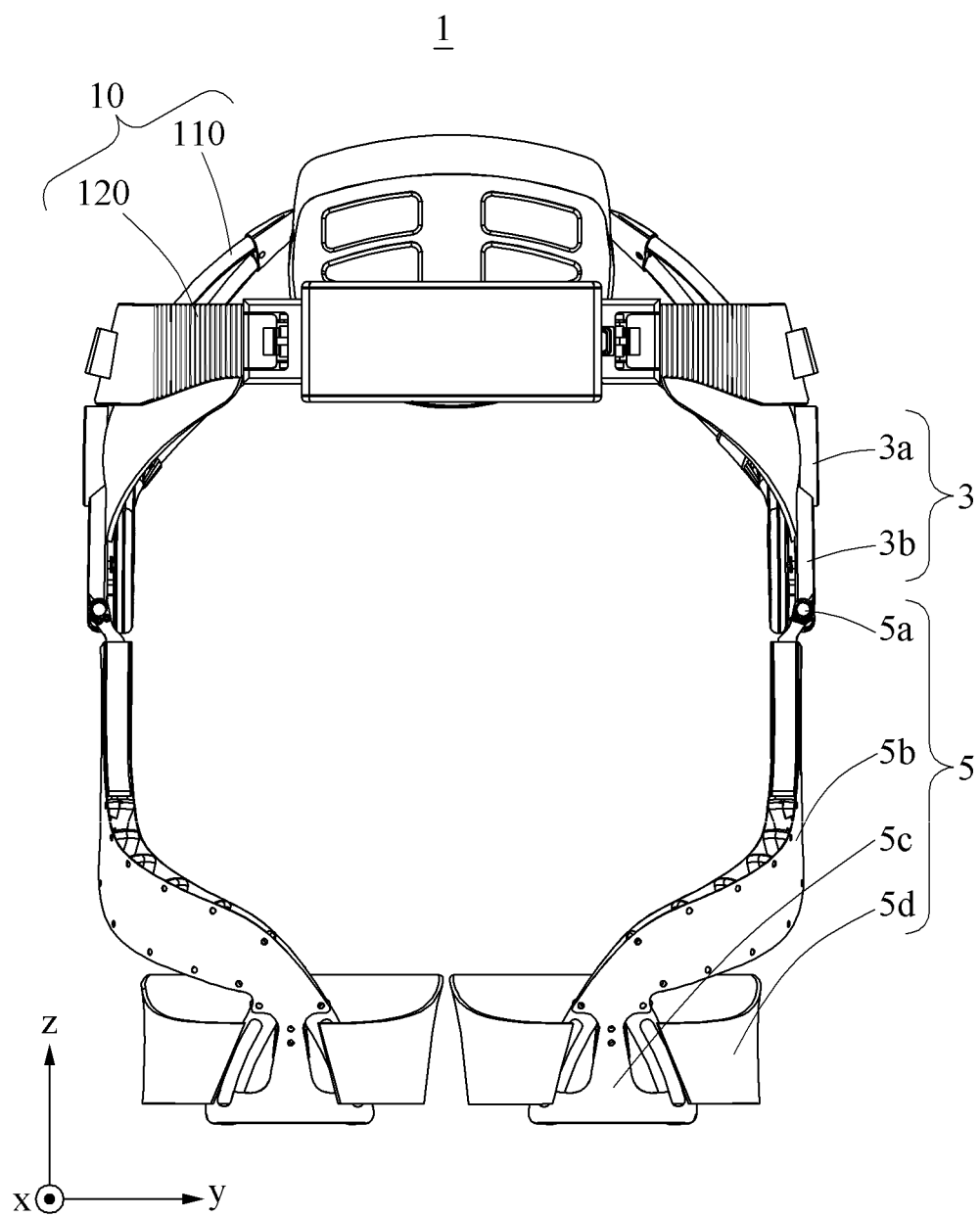
FIG. 13 is a front view illustrating a motion assistance apparatus according to at least one example embodiment.
Figure 14:
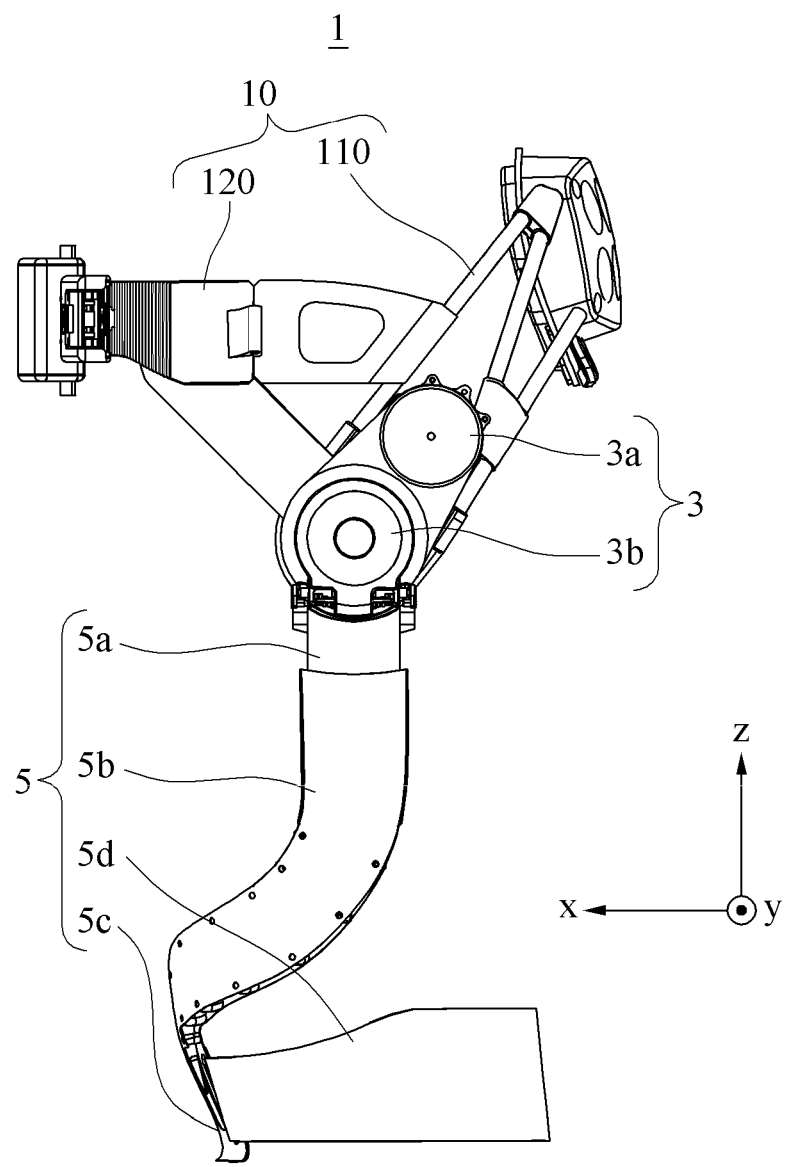
FIG. 14 is a side view illustrating a motion assistance apparatus according to at least one example embodiment.
Figure 15:
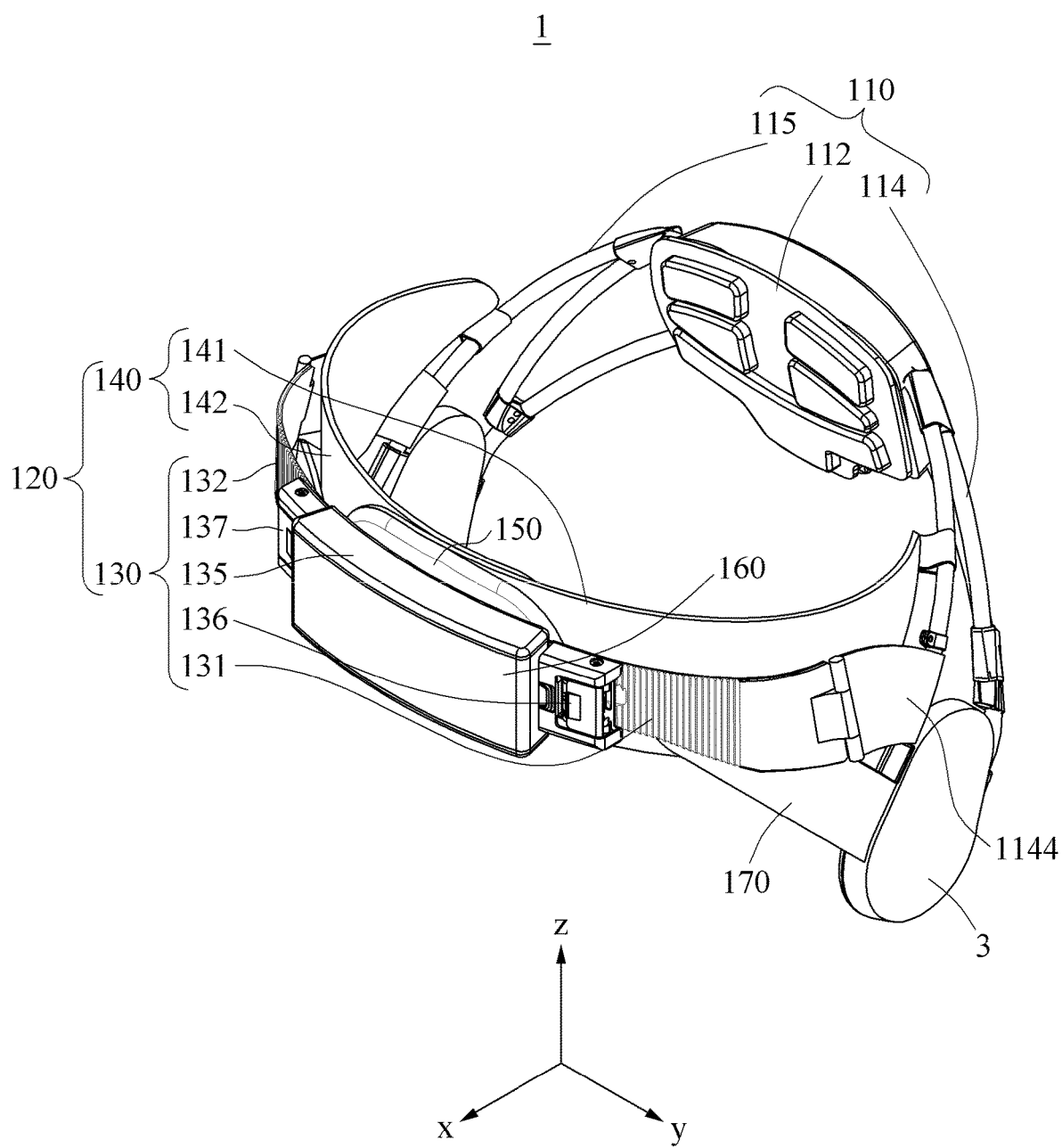
FIG. 15 is a perspective view illustrating a fixing device according to at least one example embodiment.

FIG. 13 is a front view illustrating a motion assistance apparatus according to at least one example embodiment, FIG. 14 is a side view illustrating the motion assistance apparatus according to at least one example embodiment, and FIG. 15 is a perspective view illustrating a fixing device according to at least one example embodiment. FIGS. 13 through 15 illustrate an example of a motion assistance apparatus wherein a distance maintaining member is not shown.

Referring to FIGS. 13 through 15, a motion assistance apparatus 1 includes a pelvis fixing device 10, a driving module (or, alternatively, a driver) 3, and a supporting module (or, alternatively, a support) 5.

The pelvis fixing device 10 may include a rear fixing module 110 configured to enclose a side surface and a rear surface of a waist of a user, a front fixing module 120 configured to enclose a front surface of the waist of the user, a battery 160, and an iliac crest pad 170 connected between the rear fixing module 110 and the front fixing module 120.

The rear fixing module 110 may include a back support 112 configured to support a back of the user, a first frame assembly 114, and a second frame assembly 115. The first frame assembly 114 and the second frame assembly 115 may be connected to the back support 112 and configured to extend from the back support 112 toward both sides along the side surface and the rear surface of the waist of the user. The first frame assembly 114 will be described in detail later.

The driving module 3 may include an actuator 3a and a joint assembly 3b disposed at a position corresponding to a hip joint to transmit power generated by the actuator 3a to the supporting module 5. However, example embodiments are not limited thereto. For example, the driving module 3 may transmit power to other joints of the user, for example, a knee joint and/or an ankle joint.

The supporting module 5 may support a lower limb of the user, for example, a thigh of the user, and assist a motion of the lower limb. The supporting module 5 that may rotate using a torque of the driving module 3 may include a connecting member 5a hinge-connected to the joint assembly 3b, a power transmitting frame 5b configured to slide to be connected with the connecting member 5a, an applying member 5c connected to the power transmitting frame 5b to transmit power to a portion of the user, and a supporting member 5d connected to one side of the applying member 5c to prevent a separation of the thigh of the user from the power transmitting frame 5b.

Figure 16:
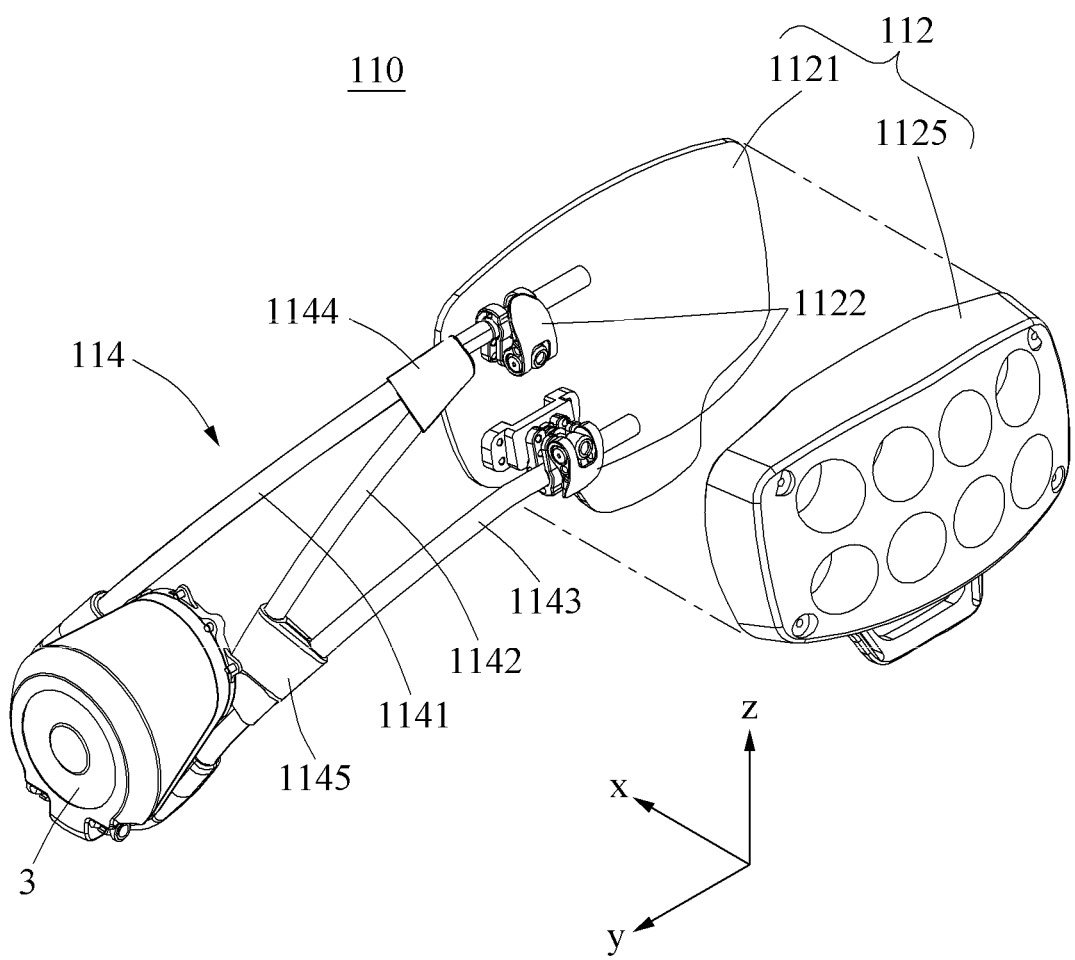
FIG. 16 is an exploded perspective view illustrating a portion of a rear fixing module according to at least one example embodiment.

FIG. 16 is an exploded perspective view illustrating a portion of a rear fixing module according to at least one example embodiment.

Referring to FIG. 16, FIG. 16 illustrates an example of the rear fixing module 110 wherein a distance maintaining member is not shown.

As discussed above, the rear fixing module 110 may include the back support 112 configured to support a back of the user, the first frame assembly 114, and the second frame assembly 115

The back support 112 may include a supporting board 1121, a control clamp 1122, and a cover 1125. The control clamp 1122 may be disposed between the supporting board 1121 and the cover 1125 to control an insertion depth of the first frame assembly 114 with respect to the back support 112. For example, the control clamp 1122 may selectively fix or unfix the first frame assembly 114 through a snap connection. Using the control clamp 1122, the first frame assembly 114 may be applied to users in various body sizes.

The first frame assembly 114 may include a first longitudinal member 1141, a second longitudinal member 1142, a third longitudinal member 1143, a first fixing clip 1144, and a second fixing clip 1145. The first longitudinal member 1141, the second longitudinal member 1142, and the third longitudinal member 1143 may correspond to the first longitudinal member L1, the second longitudinal member L2, and the third longitudinal member L3, respectively.

In the first frame assembly 114, both end portions may each have a stiffness higher than that of an intermediate portion with respect to a force. For example, an interval between two longitudinal members among a plurality of longitudinal members 1141, 1142, and 1143 may be determined by Equation 6 as described with reference to FIG. 3.

The first longitudinal member 1141 and the third longitudinal member 1143 may be spaced apart from each other and connect the back support 112 and the driving module 3. One end of the first longitudinal member 1141 may be fixed to the driving module 3, and the other end may be connected to the control clamp 1122.

The second longitudinal member 1142 may diagonally connect the first longitudinal member 1141 and the third longitudinal member 1143. The first fixing clip 1144 may allow the first longitudinal member 1141 and the second longitudinal member 1142 to be fixed to each other. The second fixing clip 1145 may allow the second longitudinal member 1142 and the third longitudinal member 1143 to be fixed to each other.

Each of the first longitudinal member 1141, the second longitudinal member 1142, and the third longitudinal member 1143 may be formed of a flexible material and provided in a shape of a hollow tube. Based on the aforementioned structure, a weight of the pelvis fixing device 10 may be reduced and the pelvis fixing device 10 may obtain a sufficient stiffness.

Figure 17:
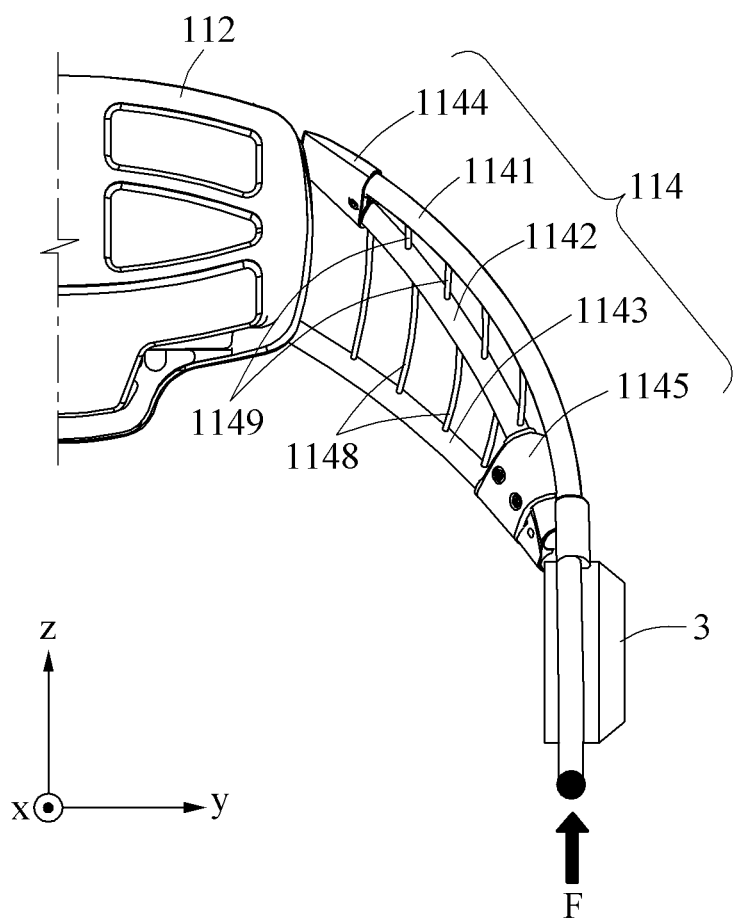
FIG. 17 is a front view illustrating a portion of a rear fixing module according to at least one example embodiment.
Figure 18:
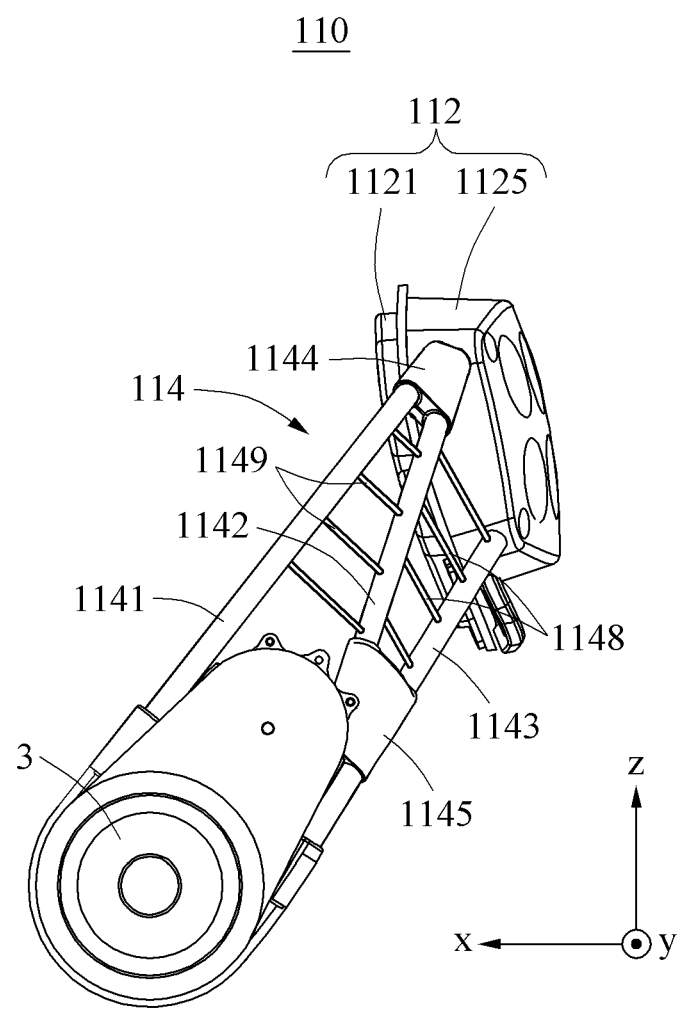
FIG. 18 is a side view illustrating a portion of a rear fixing module according to at least one example embodiment.
Figure 19:
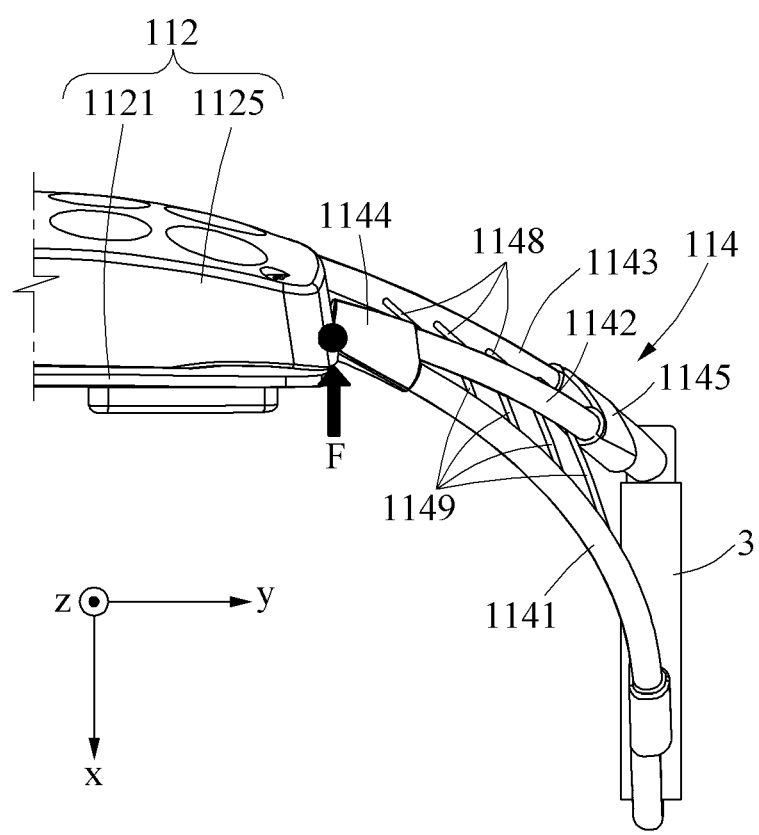
FIG. 19 is a top view illustrating a portion of a rear fixing module according to at least one example embodiment.

FIG. 17 is a front view illustrating a portion of a rear fixing module according to at least one example embodiment, FIG. 18 is a side view illustrating a portion of the rear fixing module according to at least one example embodiment, and FIG. 19 is a top view illustrating a portion of the rear fixing module according to at least one example embodiment.

Referring to FIGS. 17 through 19, the first frame assembly 114 may further include a plurality of distance maintaining members, for example, a first distance maintaining member 1148 and a second distance maintaining member 1149 configured to connect two neighboring longitudinal members among the plurality of longitudinal members 1141, 1142, and 1143. The first distance maintaining member 1148 and the second distance maintaining member 1149 may correspond to the first distance maintaining member D1 and the second distance maintaining member D2, respectively.

To increase a stiffness of the rear fixing module 110, the first distance maintaining member 1148 or the second distance maintaining member 1149 may be disposed in a different longitudinal direction in consideration of a direction of a force F applied to the rear fixing module 110.

Based on the aforementioned structure, both end portions of the first frame assembly 114 may achieve a higher stiffness with respect to a force and a moment and thus, stably support a user. Additionally, an intermediate portion of the first frame assembly 114 may achieve a flexibility that reduces a friction occurring due to a close contact with a body. Through this, both a size of the first frame assembly 114 and an inconvenience of a user may be reduced. Also, the frame assembly may not be spaced apart from the body to avoid the friction and thus, a space for accommodating the frame assembly may also decrease, which may enable a user to wear the motion assistance apparatus under clothing.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising: a back support configured to support a back of a user; a driver on one side of a joint of the user; and a frame assembly including a plurality of longitudinal members each having first ends connected to the driver and second ends connected to the back support such that a stiffness of the plurality of longitudinal members collectively increases from an intermediate portion thereof between the first ends and the second ends towards each of the first ends and the second ends, the plurality of longitudinal members including, a first longitudinal member configured to connect to back support and the driver, a second longitudinal member configured to connect to back support and the driver such that the second longitudinal member and the first longitudinal member are separated by a distance, and a third longitudinal member configured to diagonally connect the first longitudinal member and the second longitudinal member.

2. The motion assistance apparatus of claim 1, wherein the frame assembly further includes a plurality of first distance maintaining members and a plurality of second distance maintaining members, wherein the first longitudinal member and the second longitudinal member are each configured to connect to the back support and the driver; the plurality of first distance maintaining members are configured to connect the first longitudinal member and the second longitudinal member such that the second longitudinal member maintains a distance from the first longitudinal member; the third longitudinal member is configured to connect the back support and the driver; and the plurality of second distance maintaining members is configured to connect the second longitudinal member and the third longitudinal member such that the third longitudinal member maintains a distance from the second longitudinal member.

3. The motion assistance apparatus of claim 2, wherein a longitudinal direction of the plurality of first distance maintaining members intersects a longitudinal direction of the plurality of second distance maintaining members.

4. The motion assistance apparatus of claim 1, wherein each of the plurality of distance maintaining members independently extend between the driver and the back support.

5. The motion assistance apparatus of claim 4, further comprising:
a control clamp configured to control an insertion length of at least one of the first longitudinal member and the second longitudinal member into to the back support.

6. The motion assistance apparatus of claim 1, further comprising:
a plurality of distance maintaining members configured to maintain distances between corresponding ones of the plurality of longitudinal members.

7. The motion assistance apparatus of claim 6, wherein the plurality of distance maintaining members extend in a direction substantially perpendicular to a direction of at least two of the plurality of longitudinal members.

8. The motion assistance apparatus of claim 2, wherein a distance between the first longitudinal member and the second longitudinal member increases from the driver toward the back support.

9. The motion assistance apparatus of claim 8, wherein a distance between the second longitudinal member and the third longitudinal member decreases from the back support toward the driver.

10. The motion assistance apparatus of claim 2, wherein
an intermediate portion of the first longitudinal member is configured to move relative to an intermediate portion of the second longitudinal member, and
the intermediate portion of the second longitudinal member is configured to move relative to an intermediate portion of the third longitudinal member.

11. The motion assistance apparatus of claim 2, wherein the plurality of first distance maintaining members are configured to rotate relative to one or more of the first longitudinal member and the second longitudinal member.

12. The motion assistance apparatus of claim 2, wherein at least one of the plurality of first distance maintaining members is configured such that ends thereof are more flexible than an intermediate portion between the ends.

13. The motion assistance apparatus of claim 2, wherein at least one of the plurality of first distance maintaining members is configured such that cross sections of ends thereof are smaller than a cross section of an intermediate portion between the end portions.

14. The motion assistance apparatus of claim 2, wherein a thickness of at least one of the first distance maintaining members is greater than a thickness of each of the first longitudinal member and the third longitudinal member.

15. The motion assistance apparatus of claim 2, wherein at least one of the plurality of first distance maintaining members includes a first slider and a second slider, the first slider configured to slide relative to the second slider.

16. The motion assistance apparatus of claim 15, wherein
the first slider includes a first slider body connected to the first longitudinal member, and a first fitting portion on the first slider body, the first slider configured to extend toward the second longitudinal member; and
the second slider include a second slider body connected to the second longitudinal member, and a second fitting portion on the second slider body, the second slider body configured to extend toward the first longitudinal member and the second fitting portion configured to fit in the first fitting portion.

17. The motion assistance apparatus of claim 16, wherein a width of the first fitting portion increases as a distance in a direction away from the first slider body increases.

18. The motion assistance apparatus of claim 15, wherein at least one of the plurality of distance maintaining members comprises:
a separation preventing member configured to resist separation of the first slider and the second slider.

19. The motion assistance apparatus of claim 2, wherein a length of each of the plurality of first distance maintaining members is shorter than a length of the first longitudinal member and the second longitudinal member.

20. The motion assistance apparatus of claim 2, wherein, among the plurality of first distance maintaining members, a distance between two neighboring ones of the first distance maintaining members is shorter than a length of a shorter one of the two neighboring ones of the first distance maintaining members.

21. The motion assistance apparatus of claim 2, wherein at least one of the plurality of first distance maintaining members includes a material that is stiffer than a material included in the first longitudinal member and the second longitudinal member.

22. The motion assistance apparatus of claim 2, wherein at least one of the plurality of first distance maintaining members includes a first end fixed to the first longitudinal member, and a second end fixed to the second longitudinal member.

23. The motion assistance apparatus of claim 2, wherein at least one of the plurality of first distance maintaining members is rotatably fixed to one of the first longitudinal member and the second longitudinal member.

* * * * *